(12) United States Patent
Rasmussen et al.

(10) Patent No.: US 7,166,696 B2
(45) Date of Patent: Jan. 23, 2007

(54) SOLID PHASE SYNTHESIS SUPPORTS AND METHODS

(75) Inventors: Jerald K. Rasmussen, Stillwater, MN (US); Larry R. Krepski, White Bear Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/900,240

(22) Filed: Jul. 27, 2004

(65) Prior Publication Data

US 2004/0265899 A1 Dec. 30, 2004

Related U.S. Application Data

(62) Division of application No. 09/827,107, filed on Apr. 5, 2001, now Pat. No. 6,787,635.

(51) Int. Cl.
 *C07K 1/04* (2006.01)
(52) U.S. Cl. ............... 530/334; 522/113; 522/134; 524/1; 524/17
(58) Field of Classification Search ........... 530/334, 530/330; 522/113, 134; 524/1, 17
See application file for complete search history.

(56) References Cited

U.S. PATENT DOCUMENTS

| | | | |
|---|---|---|---|
| 4,350,628 A * | 9/1982 | Stammer .................... 548/228 |
| 4,639,286 A * | 1/1987 | Rasmussen et al. ...... 156/307.3 |
| 4,871,824 A | 10/1989 | Heilmann et al. |
| 4,918,231 A | 4/1990 | Krepski et al. |
| 4,996,243 A * | 2/1991 | Rasmussen et al. .......... 522/99 |
| 5,200,471 A | 4/1993 | Coleman et al. |
| 5,262,484 A | 11/1993 | Coleman et al. |
| 5,292,514 A | 3/1994 | Capecchi et al. |
| 5,336,742 A * | 8/1994 | Heilmann et al. .......... 526/260 |
| 5,344,701 A * | 9/1994 | Gagnon et al. .......... 428/304.4 |
| 5,403,902 A | 4/1995 | Heilmann et al. |
| 5,451,453 A | 9/1995 | Gagnon et al. |
| 5,486,358 A | 1/1996 | Coleman et al. |
| 5,510,421 A | 4/1996 | Dennison et al. |
| 5,561,097 A | 10/1996 | Gleason et al. |
| 5,563,220 A | 10/1996 | Webber et al. |
| 5,695,760 A * | 12/1997 | Faanes et al. ............ 424/178.1 |
| 5,726,243 A | 3/1998 | Fields |
| 5,750,245 A | 5/1998 | Exsted et al. |
| 5,907,016 A | 5/1999 | Velander et al. |
| 5,910,554 A | 6/1999 | Kempe et al. |
| 5,917,015 A | 6/1999 | Jensen et al. |
| 5,993,935 A | 11/1999 | Rasmussen et al. |

FOREIGN PATENT DOCUMENTS

| | | |
|---|---|---|
| EP | 0 801 083 A2 | 10/1997 |
| WO | WO 99/07751 A1 | 2/1999 |
| WO | WO 00/26262 A2 | 5/2000 |

OTHER PUBLICATIONS

Wang et al. "Identification of Affinity Ligands for Protein Purification from Synthetic Chemical Combinatorial Libraries" *Biotechnol. Prog.* 2002, vol. 18, pp. 524-529.

Hermanson et al. "Preparation and use of immunoglobulin-binding affinity supports on Emphaze beads" *Journal of Chromatography A*, vol. 691 (1995) pp. 113-122.

Grabski et al., "Immobilization of Manganese Peroxidase from Lentinula edodes on Alkylaminated Emphaze™ AB 1 Polymer for Generation of $Mn^{3+}$ as an Oxidizing Agent" *Applied Biochemistry and Biotechnology*, vol. 60, 1996, pp. 1-17.

Drtina et al. "Highly Cross-Linked Azlactone Functional Supports of Tailorable Polarity" *Macromolecules*, 1996, vol. 29, No. 13, pp. 4486-4489.

Coleman et al. "Immobilization of Protein A at high density on azlactone-functional polymeric beads and their use in affinity chromatography" *Journal of Chromatography*, vol. 512, (1990), pp. 345-363.

* cited by examiner

*Primary Examiner*—David Lukton
(74) *Attorney, Agent, or Firm*—Jean A. Lown; Ann M. Mueting

(57) ABSTRACT

Functionalized supports and methods for solid phase synthesis. Preferably, the functionalized support is azlactone-functionalized.

23 Claims, No Drawings

SOLID PHASE SYNTHESIS SUPPORTS AND METHODS

CROSS REFERENCE TO RELATED APPLICATIONS

This application is a divisional of U.S. Ser. No. 09/827,107, filed Apr. 5, 2001, now U.S. Pat. No. 6,787,635, the disclosure of which is herein incorporated by reference.

BACKGROUND

The recent surge of interest in combinatorial chemistry and automated synthesis has created a renewed interest in polymer-supported reactions. Combinatorial chemistry is a synthetic strategy that leads to large chemical libraries by the systematic and repetitive covalent connection of a set of different "building blocks" of varying structures to each other to yield a large "library" of diverse molecules. It is particularly useful in producing polypeptides or polynucleotides that are currently of interest in the biotechnology area. Polymer-supported reactions or solid phase synthesis is the main methodology used in combinatorial chemistry.

In order to perform combinatorial chemistry in the solid phase, the starting materials are covalently bonded to a polymeric support. Reagents can then be added that react with the starting materials to yield products that are still attached to the support. The main advantage of solid phase synthesis is that the products don't need to be purified. They can be retained on the solid phase while excess reagents and byproducts are washed away. Then, by successive treatment with different reagents, new molecules are built up on the solid phase. By using a variety of starting materials it is possible to simultaneously build up a library of related compounds by using a single reagent or set of reagents. In this way many new products can be produced in a single reaction vessel.

A wide variety of materials have been developed as polymeric supports and are commercially available. Most of these materials are based on lightly crosslinked polystyrene, a relatively hydrophobic polymer. The crosslinker most commonly used has been divinylbenzene. Crosslinking improves the mechanical properties of the resin but prevents swelling of the resin, which is essential for rapid and thorough reactivity within the polymer system. The hydrophobicity of polystyrene limits its usefulness in many solvents and with many reagents. In order to overcome the problems associated with hydrophobicity, a more hydrophilic material, such as polyethylene glycol (PEG) has been coated onto or grafted to the polystyrene to make it more versatile for solid phase synthesis. This is a very expensive process and still does not completely address the problems associated with the hydrophobic polystyrene matrix. Polystyrene resins have also been crosslinked with more hydrophilic crosslinkers such as bifunctional styrene derivatized PEG chains to crosslink polystyrene in order to improve general resin performance. Improved swelling and mechanical properties have been observed with these resins. However, PEG-based crosslinkers cannot be used with strong bases or organometallic reagents; thus, their usefulness is limited. Additionally, many prior art matrices used for solid phase synthesis have generally low crosslink density and are gel-type polymers. This polymer structure, however, can lead to problems related to reagent diffusion during synthesis. Thus, new and improved resins that can be used for solid phase synthesis are needed.

The purpose of combinatorial chemistry is to generate a large library of related compounds in order to test them for a desired property. For instance, in the drug industry, there is an interest in screening a large number of related compounds for biological activity. Usually these compounds are screened after cleavage from the support. Under these circumstances, the synthesis of combinatorial libraries requires immobilization of the first building block to the support via a linker and cleavage of the compound from the linker after the library synthesis is complete.

The linker is a molecule that can be permanently attached to the support via covalent bonds and also has a reactive group capable of binding, for example, the first building block molecule of the intended synthetic library. After the first building block is attached, further groups are systematically added sequentially until a terminal building block is attached. Finally, the desired library molecules are cleaved from the linker and thus the support. Chloromethylated crosslinked polystyrene is conventionally used to immobilize carboxylic acid building blocks via an unsubstituted benzyl ester. However, these unsubstituted benzyl-type linkers require harsh cleavage conditions, usually liquid HF. There is a need for new linker-functionalized supports that are stable to the reaction conditions used to build the library molecules on the support, but are also able to form an easily cleavable bond with the library molecule under mild conditions to release those compounds at the end of the synthesis.

SUMMARY OF THE INVENTION

The present invention provides functionalized supports and methods for use for solid phase synthesis, which are useful in combinatorial chemistry, for example. Functionalized supports described herein can be in the form of a plurality of particles or a membrane, for example. Furthermore, the functionalized support can form a combinatorial library in preferred embodiments.

Generally, preferred functionalized support material (with linker incorporated therein, herein referred to as a "linker-functionalized support") of the present invention has the formula SS—[NH—$(C(R^1)(R^2))_p$—$C(R^3)(R^4)(OR^7)]_m$ wherein SS represents a support material; $R^1$, $R^2$, $R^3$, and $R^4$ are each independently hydrogen or an organic group (preferably, a (C1–C14)alkyl group, a (C3–C14)cycloalkyl group, or a (C5–C12)aryl group) with the proviso that at least one of $R^3$ and $R^4$ is an aromatic group (preferably, a (C5–C12)aryl group); $R^7$ is hydrogen or an organic group (preferably, including a reactive site, which may optionally be protected by a protecting group); p is at least 1 (preferably, 1 to 20, and more preferably, 1 to 2); and m is 1 to the resin capacity of the support material. Typically and preferably, the NH—$(C(R^1)(R^2))_p$—$C(R^3)(R^4)(OR^7)$ groups are bound to the support material through a carbonyl group.

Alternatively, preferred functionalized support material (with linker incorporated therein) of the present invention has the formula SS—[C(O)—NH—$C(R^5)(R^6)$—$(CH_2)_n$—C(O)—NH—$(C(R^1)(R^2))_p$—$C(R^3)(R^4)(OR^7)]_m$ wherein SS represents a support material; $R^1$, $R^2$, $R^3$, and $R^4$ are each independently hydrogen or an organic group (preferably, a (C1–C14)alkyl group, a (C3–C14)cycloalkyl group, or a (C5–C12)aryl group) with the proviso that at least one of $R^3$ and $R^4$ is an aromatic group (preferably, a (C5–C12)aryl group); $R^5$ and $R^6$ are each independently an organic group (preferably, a (C1–C14)alkyl group, a (C3–C14)cycloalkyl group, or a (C5–C12)aryl group); $R^7$ is hydrogen or an organic group (preferably, including a reactive site, which may optionally be protected by a protecting group); n is 0 to 1; p is at least 1 (preferably, 1 to 20, and more preferably, 1 to 2); and m is 1 to the resin capacity of the support material. This material is a preferred example of an azlactone-functionalized support material having a linker attached thereto, wherein $C(O)$—NH—$C(R^5)(R^6)$—$(CH_2)_n$—$C(O)$ is derived from an azlactone group.

Yet another preferred functionalized support material (with linker incorporated therein) of the present invention has the formula SS—[$C(O)$—NH—$C(R_5)(R^6)$—$(CH_2)_n$—$C(O)$—NH—$(R^8)$—NH—$C(O)$—$R^9$]$_m$ wherein SS represents a support material; $R^5$, $R^6$, and $R^9$ are each independently an organic group; $R^8$ is an organic connecting group; n is 0 to 1; and m is 1 to the resin capacity of the support material. Preferably, $R^9$ includes a reactive site, which may optionally be protected by a protecting group. Preferably, $R^5$ and $R^6$ are independently a (C1–C14)alkyl group, a (C3–C14)cycloalkyl group, or a (C5–C12)aryl group), and $R^8$ is a (C1–C1000)alkylene group. This material is a preferred example of an amine-modified-azlactone-functionalized support material having a linker attached thereto, wherein NH—$(R^8)$—NH is derived from a diamine.

Use of the functionalized support materials in solid phase synthesis (typically, solid phase organic synthesis) typically requires that the support material includes a linker with a reactive site at which one or more reactions (e.g., synthetic organic reactions) can be conducted. For example, linker-functionalized supports can be used in building polynucleotides and polypeptides, which can then be released from the linker-functionalized supports. They can also be used in developing combinatorial libraries by the systematic and repetitive covalent connection of a set of different "building blocks" of varying structures to the reactive site of the linker.

Thus, the support materials described above can be used as the foundation on which such chemical reactions can be conducted if $R^7$ and $R^9$ include a reactive site. This reactive site can include a hydroxyl group (e.g., wherein $R^7$ is hydrogen) or an organic group capable of being derivatized. Alternatively, the reactive site of $R^7$ can be protected with a protecting group, e.g., for a hydroxyl functionality, in cases where that is needed during the step of attaching a linker molecule to the support material.

It should also be noted that the formulations of the support materials described above are used herein to refer to materials that include the final derivatized molecules prior to being removed from the linker-functionalized support. In such cases $R^7$ and $R^9$ may not include a reactive site; rather, they would include, for example, the desired polynucleotide or polypeptide or the desired set of molecules that form the combinatorial library.

The present invention also provides methods that utilize such supports as well as others. In one embodiment, the present invention provides a method of solid phase synthesis that includes providing an azlactone-functionalized support; reacting the azlactone-functionalized support with a linker molecule to form a linker-functionalized support having a linker attached to the azlactone-functionalized support; and conducting one or more reactions on the linker functionalized support. Preferably, this latter step involves reacting the linker-functionalized support with an organic molecule to form a covalent bond between the linker and the organic molecule; and conducting one or more reactions on the covalently bound organic molecule to produce a derivatized organic molecule. The organic molecule is preferably a building block for a combinatorial library. Typically and preferably, the covalent bond formed between the linker and the organic molecule can be cleaved under mild conditions, such as, for example, the use of mild acids or bases, as is well known to those of skill in the art of solid phase synthesis. Thus, typically and preferably, the method involves cleaving the derivatized molecule from the linker-functionalized support at the site of the covalent attachment to the linker.

Preferably, in the method described above, the linker-functionalized support has the following formula SS—[$C(O)$—NH—$C(R_5)(R^6)$—$(CH_2)_n$—$C(O)$—NH—$(C(R^1)(R^2))_p$—$C(R^3)(R^4)(OR^7)$]$_m$ wherein SS represents a support material; $C(O)$—NH—$C(R^5)(R^6)$—$(CH_2)_n$—$C(O)$ is derived from an azlactone group, wherein $R^5$ and $R^6$ are each independently an organic group and n is 0 to 1; NH—$(C(R^1)(R^2))_p$—$C(R^3)(R^4)(OR^7)$ represents the linker, wherein $R^1$, $R^2$, $R^3$, and $R^4$ are each independently hydrogen or an organic group with the proviso that at least one of $R^3$ and $R^4$ is an aromatic group, $R^7$ is hydrogen, a protecting group (e.g., for an OH functional group), or an organic group capable of being derivatized, and p is at least 1 (preferably, 1 to 20, and more preferably, 1 to 2); and m is 1 to the resin capacity of the support material. In the methods using this material, reactions occur at the —$OR^7$ group.

In another preferred embodiment of the method described above, the linker-functionalized support has the following formula SS—[$C(O)$—NH—$C(R_5)(R^6)$—$(CH_2)_n$—$C(O)$—NH—$(R^8)$—NH—$C(O)$—$R^9$]$_m$ wherein SS represents a support material; $C(O)$—NH—$C(R^5)(R^6)$—$(CH_2)_n$—$C(O)$ is derived from an azlactone group, wherein $R^5$ and $R^6$ are each independently an organic group and n is 0 to 1; NH—$(R^8)$—NH is derived from a diamine, wherein $R^8$ is an organic connecting group; $C(O)$—$R^9$ represents the linker, wherein $R^9$ is an organic group; and m is 1 to the resin capacity of the support material. In the methods using this material, reactions occur at the —$R^9$ group.

Another preferred method of the present invention includes providing an amine-odified-azlactone-functionalized support; reacting the amine-modified-azlactone-functionalized support with a linker molecule to form a linker-functionalized support having a linker attached to the amine-modified-azlactone-functionalized support; and conducting one or more reactions on the linker-functionalized support. Preferably, conducting one or more reactions on the linker-functionalized support includes reacting it with an organic molecule to form a covalent bond between the linker and the organic molecule; and conducting one or more reactions on the covalently bound organic molecule to produce a derivatized organic molecule. Typically and preferably, the covalent bond formed between the linker and the organic molecule can be cleaved under mild conditions, such as, for example, the use of mild acids or bases, as is well known to those of skill in the art of solid phase synthesis. Thus, typically and preferably, the method involves cleaving the derivatized molecule from the linker-functionalized support at the site of the covalent attachment to the linker.

In yet another preferred embodiment, the present invention provides a method of solid phase synthesis that includes providing a linker-functionalized support having the formula SS—[NH—$(C(R^1)(R^2))_p$—$C(R^3)(R^4)(OR^7)$]$_m$ wherein SS represents a support material; NH—$(C(R^1)(R^2))_p$—$C(R^3)(R^4)(OR^7)$ represents a linker, wherein $R^1$, $R^2$, $R^3$, and $R^4$ are each independently hydrogen or an organic group with the proviso that at least one of $R^3$ and $R^4$ is an aromatic group, $R^7$ is hydrogen, a protecting group, or an organic group capable of being derivatized, and p is at least 1; and m is 1 to the resin capacity of the support material; and conducting one or more reactions on the linker-functionalized support. Preferably, this involves reacting the linker-functionalized support with an organic molecule so as to form a covalent bond between the linker and the organic molecule; and conducting one or more reactions on the covalently bound organic molecule to produce a derivatized organic molecule. Typically and preferably, the covalent bond formed between the linker and the organic molecule can be cleaved under mild conditions, such as those described above. Typically and preferably, the method involves cleaving the derivatized molecule from the linker-functionalized support.

Another preferred embodiment of the methods of the present invention includes providing an azlactone-functionalized support having a linker attached thereto, which has the formula SS—[C(O)—NH—C(R5)(R$^6$)—(CH$_2$)$_n$—C(O)—NH—(C(R$^1$)(R$^2$))$_p$—C(R$^3$)(R$^4$)(OR$^7$)]$_m$ wherein SS represents a support material; C(O)—NH—C(R$^5$)(R$^6$)—(CH$_2$)$_n$—C(O) is derived from an azlactone group, wherein R$^5$ and R$^6$ are each independently an organic group and n is 0 to 1; NH—(C(R$^1$)(R$^2$))$_p$—C(R$^3$)(R$^4$)(OR$^7$) represents the linker, wherein R$^1$, R$^2$, R$^3$, and R$^4$ are each independently hydrogen or an organic group with the proviso that at least one of R$^3$ and R$^4$ is an aromatic group, R$^7$ is hydrogen, a protecting group, or an organic group capable of being derivatized, and p is at least 1; and m is 1 to the resin capacity of the support material; reacting the linker with an organic molecule to form a covalent bond between the linker and the organic molecule; conducting one or more reactions on the covalently bound organic molecule to produce a derivatized organic molecule; and cleaving the derivatized molecule from the azlactone-functionalized support having a linker attached thereto.

Yet another preferred embodiment of the methods of the present invention includes providing a linker-functionalized support having the formula SS—[C(O)—NH—C(R5)(R$^6$)—(CH$_2$)$_n$—C(O)—NH—(R$^8$)—NHC(O)—R$^9$]$_m$ wherein SS represents a support material; C(O)—NH—C(R$^5$)(R$^6$)—(CH$_2$)$_n$—C(O) is derived from an azlactone group, wherein R$^5$ and R$^6$ are each independently an organic group and n is 0 to 1; NH—(R$^8$)—NH is derived from a diamine, wherein R$^9$ is an organic connecting group; C(O)—R$^9$ represents the linker, wherein R$^9$ is an organic group; and m is 1 to the resin capacity of the support material; reacting the linker with an organic molecule so as to form a covalent bond between the linker and the organic molecule; conducting one or more reactions on the covalently bound organic molecule to produce a derivatized organic molecule; and cleaving the derivatized molecule from the azlactone-functionalized support having a linker attached thereto.

Whether directed to a method or a support, the present invention includes the following preferred embodiments he functionalized support can be in the form of a plurality of particles. Each R$^7$ (or R$^9$) can be the same on any one particle, or the plurality of particles can include at least two different R$^7$ (or R$^9$) groups. Alternatively, the functionalized support can be in the form of a membrane. Each R$^7$ (or R$^9$) can be the same on the membrane, or the membrane can include at least two different R$^7$ (or R$^9$) groups.

DEFINITIONS

An "organic molecule" (i.e., the starting material) can be a monomer, oligomer, or polymer, although typically it is a monomer. These can be used as the "building blocks" in combinatorial chemistry. A "derivatized organic molecule" is an organic molecule that is different in some way relative to the starting organic molecule. The organic molecule and derivatized organic molecule can include heteroatoms and substituents as described below with respect to the definition of "organic group." Herein, an organic molecule can also include metals or metalloids, such that it could be classified as an organometallic molecule.

The term "organic group" means a hydrocarbon group (with optional elements substituted for carbon and hydrogen, such as oxygen, nitrogen, sulfur, and silicon) that is classified as an aliphatic group, cyclic group, or combination of aliphatic and cyclic groups (e.g., alkaryl and aralkyl groups). In the context of the present invention, the organic groups are those that do not interfere with chemical reactions that occur at the reactive site of the linker, such as occur in the formation of a derivatized organic molecule. The term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and recitation of certain terminology used throughout this application, the terms "group" and "moiety" are used to differentiate between chemical species that allow for substitution or that may be so substituted and those that do not allow or may not be so substituted. Thus, when the term "group" is used to describe a chemical substituent, the described chemical material includes the unsubstituted group and that group with O, N, Si, or S atoms, for example, in the chain (as in an alkoxy group) as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like. A "hydrocarbyl moiety" refers to an organic moiety containing only carbon and hydrogen atoms (no substituents or heteroatoms).

The term "organic connecting group" means an "organic group" which is situated between and joins at least two chemically reactive groups. In the case of the present invention this term is used preferably to represent the "organic group" which joins two or more amino groups.

The term "linker molecule" refers to a molecule that can be permanently attached to a support material via covalent bonds to form a "linker". The linker molecule (and linker) includes a reactive group capable of binding an organic molecule, which then can be derivitized and cleaved from the support material. Herein, linker molecule refers to the species prior to being attached to the support material and linker refers to the species after it has been attached to the support material.

The term "mild conditions" as it applies to cleavage of the covalent bond formed between the linker and the organic molecule refers to conditions that do not degrade, or otherwise affect, the derivatized organic molecule, but just removes it from the functionalized support. In general, these are conditions well known in the art of solid phase synthesis.

The term "resin capacity" or "functional group density" means a measure of the amount of functionality of the support material (typically, in the form of a resin), typically described in units such as moles/gram or equivalents/gram of resin.

DETAILED DESCRIPTION OF PREFERRED EMBODIMENTS

The present invention provides functionalized supports and methods for use for solid phase synthesis (typically, solid phase organic synthesis), for example. These functionalized supports can be used for synthesizing small molecules as well as large molecules (e.g., biomolecules). Significantly, the functionalized support can be used in solid phase synthesis in which, for example, organic molecules (e.g., monomers) are consecutively added to a chain or polymer, as occurs in the formation of polypeptides, polynucleotides, etc., including peptidomimetics. The functionalized support can also be used to form a combinatorial library if desired, which is of significant interest in a variety of fields, particularly the pharmaceutical industry.

Support Material

Functionalized supports include a support material (often referred to as a base support or base polymer or base resin) and one or more functional groups, preferably, azlactone functional groups. The support material can be a pre-existing material to which functional groups, preferably, azlactone functional groups, are attached (e.g., through the use of high energy radiation and free radical reactions), or the support material and functionalization thereof can occur generally simultaneously (e.g., through the use of free radical polymerization).

The support material can be a polymeric material that can be used in conventional solid phase synthesis. It is chosen such that it is generally insoluble in the solvents or other components used in synthetic reactions that occur during the course of solid phase synthesis.

The support material can be organic or inorganic. It can be in the form of solids, gels, glasses, etc. It can be in the form of a plurality of particles (e.g., beads, pellets, or microspheres), fibers, a membrane (e.g., sheet or film), a disc, a ring, a tube, or a rod, for example. Preferably, it is in the form of a plurality of particles or a membrane. It can be swellable or nonswellable. It can be porous or nonporous. It can be pre-existing or made in situ (such that functionalization occurs during formation of the support material). Preferably, it is made in situ, as occurs in the formation of vinyl azlactone/methylenebisacrylamide copolymer beads.

Examples of useable pre-existing support materials are described in G. B. Fields et al., *Int. J. Peptide Protein Res.*, 35, 161 (1990) and G. B. Fields et al., in *Synthetic Peptides: A User's Guide*, G. A. Grant, Ed., pages 77–183, W. H. Freeman and Co., New York, N.Y. (1992). Preferably, the support material is in the form of an organic polymeric material, such as polystyrenes, polyalkylenes, nylons, polysulfones, polyacrylates, polycarbonates, polyesters, polyimides, polyurethanes, etc. For pre-existing support materials, a preferred support material is polystyrene. Included in the term "polystyrene" are polymers that have been substituted to some extent with substituents that are not capable of reaction under the conditions generally used for solid phase synthesis of biomolecules, e.g., substituents such as alkyl and alkoxy groups. In order to increase the stability and insolubility in organic solvents, polystyrene resins are typically crosslinked with, for example, divinyl benzene or butadiene.

Functionalized Supports

Preferably, the support material includes functional groups to which linker molecules can be attached for building large or small organic compounds. Suitable functional groups include electrophilic groups such as epoxide or oxirane groups, N-hydroxysuccinimide ester groups, sulfonyl ester groups, iodoacetyl groups, aldehyde groups, imidazolylcarbamate groups, chlorotriazine groups, or other groups capable of reacting to form covalent bonds with linker molecules, particularly those linker molecules containing amino groups.

In one preferred embodiment, the functional groups are azlactone groups.

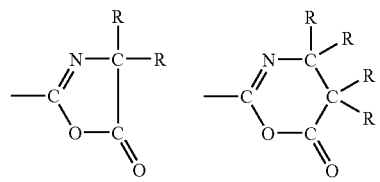

Azlactone-functionalized supports have been described in U.S. Pat. No. 5,403,902 (Heilmann et al.), for example. They are described as being useful reactive supports for the attachment of functional materials to provide adduct beads. The adduct beads are useful as complexing agents, catalysts, polymeric reagents, chromatographic supports, and as enzyme- or other biomacromolecule-bearing supports. Azlactone beads have high binding capacity with functional materials even when the beads are highly crosslinked and swell very modestly, e.g., threefold or less, in water.

It has now been found that azlactone-functionalized supports, such as these, can be reacted with a linker molecule to form a linker which can be further reacted with a building block molecule (i.e., organic molecules typically used in combinatorial chemistry to build larger molecules such as polypeptides and polynucleotides) through a covalent bond. With certain linkers the covalent bond is cleavable under mild conditions. The building block molecule can then be subjected to numerous chemical reactions using, for example, a combinatorial synthetic scheme to produce a library of compounds attached to the support via the linker. When the covalent bond between the linker and the covalently bound building block molecule is cleaved under mild conditions, the library of organic compounds is released, regenerating the active support (i.e., the functionalized support with linkers attached thereto).

Particularly preferred azlactone-functionalized supports include vinyl azlactone copolymers, such as those described in U.S. Pat. No. 5,403,902 (Heilman et al.). Most preferred azlactone-functionalized supports are vinyl azlactone/methylenebisacrylamide copolymers, such as those commercially available under the trade designation EMPHAZE AB 1 from Minnesota Mining and Manufacturing Company (St. Paul, Minn.) or ULTRALINK Biosupport Medium from Pierce Scientific (Rockford, Ill.). These copolymers are extremely stable to strongly acidic and basic conditions, and thus are ideal base supports for solid phase synthesis.

Typically and preferably, linker molecules can be added to such functionalized supports to create reactive sites for solid phase synthesis. The term "linker molecule" refers to a molecule that can be permanently attached to a support material via covalent bonds to form a "linker". The linker molecule (and linker) includes a reactive group capable of binding an organic molecule, which then can be derivitized and cleaved from the support material, if desired.

The linker is preferably chemically stable to the reaction conditions necessary to derivatize the organic molecule (e.g., and build a combinatorial library). It also preferably is chosen to allow the synthesized molecules to be easily cleaved from the support. The linker may include a protecting group (e.g., a hydroxylprotecting group) at the reactive site, if desired, which can be removed prior to conducting the desired chemical reactions for building larger molecules, for example.

Preferred linker molecules include, but are not limited to, aminoalcohols having the structure $H_2N-(C(R^1)(R^2))_p-C(R^3)(R^4)-OH$, such as 2-amino-1-phenylethanol, 2-amino-1-(4-methoxyphenyl)ethanol, 2-amino-1-methyl-1-phenylethanol, 2-amino-1,1-diphenylethanol, 3-amino-1-phenylpropanol, 2-amino-1-phenylpropanol, and the like. Such molecules are readily prepared by cyanosilylation/reduction of aldehydes and ketones as described in Evans et al., *J. Org. Chem.*, 39, 914 (1974) and in U.S. Pat. No. 4,918,231 (Krepski et al.). These linker molecules provide benzylic alcohol functionality similar to the familiar Wang and Rink linkers (described, for example, in Wang, *J. Amer. Chem. Soc.*, 95, 1328 (1973) and Rink, *Tetrahedron Letters*, 28, 3787 (1987)) commonly used in solid phase synthesis, but in addition contain amine functionality useful for providing stable amide bonds to the support material.

Optically active amino alcohols are other examples of linker molecules. They offer the possibility of conducting asymmetric synthetic transformations on the attached organic molecule. Specific, well-known examples include erythro-alpha-(1-aminoethyl)benzyl alcohol (also known as (1S,2R)-(+)-norephedrine), (R)-(−)-norepinephrine, (S)-(+)-norepinephrine, L-erythro-2-(methylamino)-1-phenylpropanol (aka l-ephedrine), D-threo-2-(methylamino)-1-phenylpropanol (also known as d-pseudoephedrine), and d-2-amino-1-phenylethanol.

In addition to the preferred linker molecules described above, many of the traditional linker molecules commonly utilized for solid phase synthesis can also be used with azlactone-functionalized supports provided that these supports are suitably derivatized to allow attachment of the traditional linker molecules. Preferably, this derivatization process involves reaction of the azlactone group with an excess of a polyamine, to produce an amine-modified-azlactone-functionalized support. Examples of polyamines include primary polyamines, such as ethylenediamine, 1,3-propanediamine, 1,3-diamino-2-hydroxypropane, 1,6-hexanediamine, tris-(2-aminoethyl)amine, and the like; and polyetherpolyamines, such as 4,7,10-trioxa-1,13-tridecanediamine, 3,6-dioxa-1,8-diaminooctane, amine-terminated polyethyleneglycol and polypropyleneglycol homopolymers and copolymers; and the like. Preferably, the polyamines are diamines, such as ethylenediamine, 1,3-propanediamine, 1,3-diamino-2-hydroxypropane, or 1,6-hexanediamine. In a second step, carboxyl functional linker molecules can be reacted with the amine to form an amide bond to the support. Examples of suitable linker molecules include, but are not limited to, 4-hydroxymethylbenzoic acid, 4-hydroxymethylphenoxyacetic acid, 4-hydroxymethyl-3-methoxyphenoxybutyric acid, 4-hydroxymethylphenylacetic acid, 4-bromoacetylphenoxyacetic acid, 4-(diphenylhydroxymethyl)benzoic acid, 4-hydroxymethyl-2-methoxy-5-nitrophenoxybutyric acid, phenoxyacetic acid and phenoxybutyric acid analogs of Rink acid and Rink amide linker molecules and Sieber amide linker molecules (described, for example, in Rink, *Tetrahedron Letters*, 28, 3787 (1987) and Sieber, *Tetrahedron Letters*, 28, 2107 (1987)), 4-sulfamylbenzoic acid, 4-sulfamylbutyric acid, 4-formylphenoxyacetic acid, 4-(4-formyl-3-methoxyphenoxy)butyric acid, 4-formyl-3,5-dimethoxyphenoxyacetic acid, 3-formylindol-1-ylacetic acid, and the like. This synthetic scheme preferably results in a resin of the general structure $SS-[C(O)-NH-C(R^5)(R^6)-(CH_2)_n-C(O)-NH$-(organic group from amine)-$NH-C(O)$-linker$]_m$.

The linker molecules can be attached to the support material using conventional attachment chemistry, such as carbodiimide chemistry, mixed anhydride chemistry, and the like. Such techniques are well known to one of skill in the art.

Once attached to the functionalized support, the linker provides one or more reactive sites for subsequent reaction, such as those that occur in solid phase synthesis (typically, organic synthesis). Such functionalized supports having a linker attached thereto are referred to herein as linker-functionalized supports. The reactive site can include a hydroxyl group or an organic group capable of being derivatized. Alternatively, the reactive site can be protected by a protecting group, e.g., for a hydroxyl functionality, in cases where that is needed during the step of attaching a linker molecule to the support material. Examples of such protecting groups include t-butyldimethylsilyl, triphenylmethyl, and others well known in the art (see, for example, Harrison and Harrison, *Compendium of Organic Synthetic Methods*, pages 124–131, John Wiley and Sons, New York, 1971). Such protecting groups are removed during the process of conducting reactions on the linker.

It should also be noted that the formulations of the support materials described herein are used herein to refer to materials that include the final derivatized molecules prior to being removed from the linker-functionalized support. In such cases the linkers (which include, for example $R^7$ and $R^9$ in the formulations herein) may not include a reactive site; rather, they would include, for example, the desired polynucleotide or polypeptide or the desired set of molecules that form the combinatorial library. As a result they can be quite large.

Preferably, a linker-functionalized support has the following formula $SS-[C(O)-NH-C(R_5)(R^6)-(CH_2)_n-C(O)-NH-(C(R^1)(R^2))_p-C(R^3)(R^4)(OR^7)]_m$ wherein SS represents a support material; $R^1$, $R^2$, $R^3$, and $R^4$ are each independently hydrogen or an organic group (preferably, having up to about 20 carbon atoms) with the proviso that at least one of $R^3$ and $R^4$ is an aromatic group; $R^7$ is hydrogen or an organic group; $R^5$ and $R^6$ are each independently an organic group (preferably, having up to about 20 carbon atoms); n is 0 to 1; p is at least 1 (preferably, 1 to 20, and more preferably, 1 to 2); and m is 1 to the resin capacity of the support material. Preferably, C(O)—NH—C($R^5$)($R^6$)—($CH_2$)$_n$—C(O) is derived from an azlactone group and NH—(C($R^1$)($R^2$))$_p$—C($R^3$)($R^4$)(O$R^7$) represents the linker. Preferably, when O$R^7$ is the attachment site for an organic molecule, $R^7$ is hydrogen or an organic group capable of being derivatized, as in combinatorial chemistry, for example. Alternatively, the organic group could be a protecting group for, e.g., a hydroxyl functionality, in cases where that is needed during the step of attaching the linker to the support. Prior to any reactions being conducted on the linker-functionalized support, the protecting group is removed. For certain embodiments, $R^7$ can include the final desired product. As a result it can be quite large, including polynucleotides and polypeptides, for example.

Another preferred linker-functionalized support has the following formula SS—[C(O)NH—C(Rs)($R^6$)—($CH_2$)$_n$—C(O)—NH—($R^8$)—NH—C(O)—$R^9$]$_m$ wherein SS represents a support material; $R^5$ and $R^6$ are each independently an organic group (preferably, having up to about 20 carbon atoms); $R^9$ is an organic group; $R^8$ is an organic connecting group (preferably, having up to about 1000 carbon atoms); n is 0 to 1; and m is 1 to the resin capacity of the support material. $R^8$ can be any linear or branched organic group and is preferably derived from diamines. Examples of such diamines include primary diamines, such as ethylenediamine, 1,3-propanediamine, 1,3-diamino-2-hydroxypropane and 1,6-hexanediamine, and the like; and polyetherdiamines, such as 3,6-dioxa-1,8-diaminooctane, amine-terminated polyethyleneglycol and polypropyleneglycol homopolymers and copolymers; and the like. Preferably, C(O)—NH—C($R^5$)($R^6$)—($CH_2$)$_n$—C(O) is derived from an azlactone group, NH—($R^8$)—NH is derived from a diamine, and C(O)—$R^9$ represents the linker. Preferably, NH—($R^8$)—NH is derived from ethylenediamine, 1,3-propanediamine, 1,3-diamino-2-hydroxypropane, or 1,6-hexanediamine.

Preferably, when C(O)—$R^9$ is the linker, it includes an attachment site for an organic molecule. Such attachment sites can be the same as those described above for $R^7$ (e.g., hydroxyl group, an organic group capable of being derivatized, or a protecting group). Preferably, C(O)—$R^9$ is derived from 4-hydroxymethylbenzoic acid, 4-hydroxymethylphenoxyacetic acid, 4-hydroxymethyl-3-methoxyphenoxybutyric acid, 4-hydroxymethylphenylacetic acid, 4-bromoacetylphenoxyacetic acid, 4-(diphenylhydroxymethyl)benzoic acid, 4-hydroxymethyl-2-methoxy-5-nitrophenoxybutyric acid, phenoxyacetic acid and phenoxybutyric acid analogs of Rink acid and Rink amide linker molecules and Sieber amide linker molecules, 4-sulfamylbenzoic acid, 4-sulfamylbutyric acid, 4-formylphenoxyacetic acid, 4-(4-formyl-3-methoxyphenoxy)butyric acid, 4-formyl-3,5-dimethoxyphenoxyacetic acid, or 3-formylindol-1-ylacetic acid. For certain embodiments, $R^9$ can include the final desired product. As a result it can be quite large, including polynucleotides and polypeptides, for example.

Alternatively, a linker-functionalized support does not necessarily have to be derived from azlactone functionality, but can have the following formula SS—[NH—(C($R^1$)($R^2$))$_p$—C($R^3$)($R^4$)(O$R^7$)]$_m$ wherein SS represents a support material; $R^1$, $R^2$, $R^3$, and $R^4$ are each independently hydrogen or an organic group with the proviso that at least one of $R^3$ and $R^4$ is an aromatic group; $R^7$ is hydrogen or an organic group; p is at least 1 (preferably, 1 to 20, and more preferably, 1 to 2); and m is 1 to the resin capacity of the support material. Preferably, NH—(C($R^1$)($R^2$))$_p$—C($R^3$)($R^4$)(O$R^7$) represents a linker. It is typically attached to the support material through a carbonyl group, thereby forming an amide linkage. Preferably, when O$R^7$ is the attachment site for an organic molecule, $R^7$ is hydrogen, an organic group capable of being derivatized, or a protecting group, which would be removed prior to any reactions being conducted on the linker-functionalized support. More preferably, $R^7$ is hydrogen. For certain embodiments, $R^7$ can include the final desired product. As a result it can be quite large, including polynucleotides and polypeptides, for example.

When the functionalized supports include organic groups at the $R^1$, $R^2$, $R^3$, $R^4$, $R^5$, $R^6$ and $R^8$ positions, these can be of any size or functionality that do not interfere with the solid phase synthesis reactions. Preferably, $R^1$, $R^2$, $R^3$, $R^4$, $R^5$, and $R^6$ are each independently alkyl groups (preferably, containing 1 to 14 carbon atoms, and more preferably (C1–C14)alkyl moieties) or cycloalkyl groups (preferably, containing 3 to 14 carbon atoms, and more preferably (C3–C14)cycloalkyl moieties), aryl groups (preferably, containing 5 to 12 ring atoms, and more preferably (C5–C12) aryl moieties). Preferably, at least one of $R^3$ and $R^4$ is an aryl group (preferably, containing 5 to 12 ring atoms). Any two of the groups $R^1$ and $R^2$ or $R^5$ and $R^6$ taken together with the carbon to which they are joined can form a carbocyclic ring, preferably containing 4 to 12 ring atoms. Preferably, $R^8$ is an alkylene group (more preferably, an alkylene moiety) having up to about 1000 carbon atoms.

Functionalized supports (including linker-functionalized supports) of the present invention can have the same or mixtures of functional groups and/or linkers. For example, support materials as described herein can include at least two different $R^7$ (or $R^9$) groups. If particles are used, this can result from blending two different samples of particles, each with a different $R^7$ (or $R^9$) group. Alternatively, a membrane can include at least two different $R^7$ (or $R^9$) groups.

Base functionalized supports can be prepared by methods well known in the art, and many are available commercially (e.g., from various companies such as Novabiochem, BiO-Rad, Pierce, Amersham-Pharmacia, Rapp Polymere, Polymer Laboratories, Sigma-Aldrich, Millipore, EM Separations, etc.). Methods for the preparation of azlactone-functionalized supports are described, for example, in U.S. Pat. No. 5,403,902 (Heilmann et al.). This patent describes the preparation of particulate supports by suspension or dispersion polymerization processes. Other methods for preparing useful azlactone-functionalized supports are described in U.S. Pat. No. 5,262,484 (Coleman et al.), which describes graft copolymers and articles prepared therefrom, U.S. Pat. No. 5,292,514 (Capecchi et al.), which describes functionalized substrates, U.S. Pat. No. 5,451,453 (Gagnon et al.), which describes porous supports, U.S. Pat. No. 5,486,358 (Coleman et al.), which describes polymer blends and articles prepared therefrom, U.S. Pat. No. 5,510,421 (Dennison et al.), which describes membrane supports, and U.S. Pat. No. 5,993,935 (Rasmussen et al.), which describes bead/porous matrix composites.

Use of the Functionalized Supports

The functionalized supports are preferably used to covalently attach a linker molecule and to provide a starting point for solid phase synthesis of a compound, which may or may not be polymeric. For example, in creating a combinatorial library, the functional groups with linker and organic molecule attached thereto can be divided into groups and then chemically modified by introduction of substituents to form a series of analogs. Alternatively, conventional formation of a polymer (e.g., homopolymer, copolymer, terpolymer, etc.) by stepwise addition of monomers can occur.

Conventional solid phase synthetic techniques can be used. Such synthetic techniques can include the use of protecting groups. These can be deprotected using appropriate cleavage reagents well known to those of skill in the art.

After synthesis is complete, cleavage conditions are used to remove the modified organic molecule (i.e., organic compound), preferably by cleaving the covalent bond between the linker and the organic molecule. Preferably, the cleavage conditions are mild, whether they be acidic or basic. Typically, mild conditions involve the use of acids (particularly acids having an $H_0$ of −5 or higher, as defined by J. P. Tam et al. in *The Peptides*, Vol. 9, S. Udenfreind and J. Eienhofer, Eds., pages 185–248, Academic Press, New York, N.Y. (1987)), such as hydrochloric, acetic, sulfuric, and trifluoroacetic acid. Preferably, trifluoroacetic acid is used. Basic cleavage conditions may also be used through the use of, for example, sodium hydroxide or ammonia solutions. Other useful common methods of cleavage are reviewed in numerous literature articles, for example, in "The Combinatorial Chemistry Catalog" published annually by Calbiochem-Novabiochem, San Diego, Calif.

The method of using the functionalized supports described herein is particularly useful in preparing a combinatorial library. Specifically, in making such a library, a plurality of reaction vessels are provided, each containing a functionalized support with a linker attached thereto. A different monomer, each capable of reacting with the linker on the functionalized support, is provided in each vessel. Additional monomers are coupled to the growing oligomer chain, with the identity and order of monomers documented to enable synthesis of a plurality of support-bound, chemically distinct oligomers. This last step may involve a "split/mix" approach, wherein after every monomer addition, the contents of the reaction vessels are alternatively divided and mixed in a way that provides for a completely diverse set of ligands. The distinct oligomers in the combinatorial library so provided are then screened for activity, generally by screening individual sublibraries containing mixtures of distinct oligomers, identifying active sublibraries, and then determining the oligomeric compounds of interest by generating different sublibraries and cross-correlating the results obtained.

EXAMPLES

The following examples are given to illustrate, but not limit, the scope of this invention. Unless otherwise indicated, all parts and percentages are by weight and all molecular weights are weight average molecular weights.

Example 1

Coupling of 2-amino-1-phenylethanol (Aldrich Chemical Co., Milwaukee, Wis.) to EMPHAZE AB 1 beads (Minnesota Mining and Manufacturing Company) 1 molar (1M) solutions were prepared of the aminoalcohol in (a) dimethylformamide/deionized water (12 mL/4 mL) and (b) dimethylsulfoxide/deionized water (12 mL/4 mL). To each solution was added 1.0 gram (g) AB 1 beads, and each mixture was tumbled for 3.5 hours (hrs). Workup was accomplished by filtering, washing the derivatized beads with acetone (3 times), deionized water, 0.1 normal (0.1N) HCl (2 times), then deionized water until the filtrate was neutral to pH paper. Evaluation by a cation exchange procedure for lysozyme, as described in U.S. Pat. No. 5,561,097 (Gleason et al.), indicated a 70% coupling efficiency of the linker in both reactions.

Example 2

Procedures similar to those of Example 1 were used to couple 2-amino-1-phenylethanol to 140 micrometer (μ) diameter azlactone-functional beads. Details are listed in Table 1. Lysozyme cation exchange testing was used to estimate coupling efficiency of the linker.

TABLE 1

| DMSO/water (v/v) | Time (hrs) | EEDQ[1] | Coupling Efficiency (%) |
|---|---|---|---|
| a) 4:1 | 1 | + | 33 |
| b) 4:1 | 3 | − | 29 |
| c) 1:4 | 2 | + | 62 |
| d) 1:4 | 2 | − | 70 |
| e) 1:4 | 3 | − | 78 |

[1]Reaction done in the presence (+) or absence (−) of 0.1 M 2-ethoxy-1-ethoxycarbonyl-1,2-dihydroquinoline.

Example 3

Attachment and release of benzoic acid to modified beads was accomplished using the following methods: benzoic acid was coupled to the beads of Example 2d by the procedure of Valerio et al., *Int. J. Peptide Res.*, 44, 158–165 (1994) using diisopropylcarbodiimide and 4-dimethylaminopyridine in 25/75:volume/volume (25%) $DMF/CH_2Cl_2$. Specifically, 2 milliliters (mL) of wet beads were placed in a 15 mL polypropylene disposable chromatography column and mixed with 7 mL of 1N sodium hydroxide for 1 hour. The sodium hydroxide solution was drained off and the beads were washed 3 times with 10 mL of deionized water, 3 times with 10 mL of acetone, then 2 times with 10 mL of 25% $DMF/CH_2Cl_2$ mixture. The damp beads were then mixed with a solution of 37 milligrams (mg) benzoic acid, 47 microliters (μL) diisopropyl-carbodiimide, and 4 mg 4-dimethylaminopyridine in 3 mL 25% $DMF/CH_2Cl_2$ mixture. The mix was allowed to react overnight at room temperature, filtered, and washed with 10 mL 25% $DMF/CH_2Cl_2$ mixture, 3 times with 10 mL acetone, 3 times with 10 mL ethanol, and 3 times with deionized water. The derivatized beads were mixed with 8 mL of 0.1N sodium hydroxide for 1 hour and the sodium hydroxide extract was drained off. Second and third 8 mL hydrolysis extracts were made, using 1.0N and 2.0N sodium hydroxide, respectively. Anion exchange-SR extraction disks commercially available under the trade designation EMPORE from Minnesota Mining and Manufacturing Company were preconditioned according to the manufacturer's recommendations, then a hydrolysis extract was passed through the membrane using aspirator vacuum, and the membrane was washed 2 times with deionized water. The filtration apparatus was transferred to a clean filter flask, and the membrane was eluted 2 times with 10 mL concentrated ammonia. The eluate was finally evaporated to dryness under vacuum, leaving a small amount of white residue. From the 2.0N extract, the ammonia eluate was acidified to pH 1 with concentrated hydrochloric acid, then passed through a preconditioned EMPORE C18 solid phase extraction disk. The disk was then allowed to dry for 1 hour and eluted 2 times with 10 mL acetonitrile. GC-MS analysis of the eluate residue upon evaporation indicated the presence of benzoic acid as a major component. The other extracts also contained benzoic acid. Extraction disks commercially available under the trade designation EMPORE C8 from Minnesota Mining and Manufacturing Co. were also useful for recovering the hydrolysis products.

Example 4

Benzoic acid was coupled to 1 mL of the beads of Example 2e by the procedure described in Example 3. After coupling and washing, the beads were mixed with 7 mL concentrated ammonia for 1 hour. The ammonia solution was drained off, and the ammonia hydrolysis procedure was repeated a second time. The combined ammonia solutions were evaporated under vacuum to give a white residue. GC-MS of this residue identified benzamide as the major component.

Examples 3 and 4 illustrate that the linker of Example 1 can be used to attach and subsequently release an appropriate organic molecule under mild basic hydrolysis conditions.

Example 5

2-Amino-1-(4-methoxyphenyl)ethanol was prepared according to the procedure of Evans et al., *J. Org. Chem.*, 39, 914 (1974) by cyanosilylation of 4-methoxybenzaldehyde followed by lithium aluminum hydride reduction. The crude aminoalcohol (36.9 g) was dissolved in 150 mL of hot ethanol on a steam bath. To this mixture was slowly added 12.83 g of fumaric acid. The precipitated salt was filtered and washed with additional ethanol. Recrystallization from methanol provided greater than 99% pure 2:1 amine:fumarate salt.

EMPHAZE AB 1 beads (250 mg) and the above fumarate salt (740 mg) in 4.5 mL deionized water were allowed to react for 2 hours. The derivatized beads were filtered, washed with DMSO (2 times), acetone (2 times), deionized water, 0.1N HCl, then deionized water until the filtrate was of neutral pH. Lysozyme cation exchange analysis indicated an 82% coupling efficiency. The derizatized beads were treated 3 times in succession, 1 hour each, with 4 mL volumes of 5% trifluoroacetic acid (TFA) in $CH_2Cl_2$. The beads were washed with deionized water (3 times), acetone (3 times), and 25% DMF/$CH_2Cl_2$. Benzoic acid was coupled to these beads using a procedure similar to that of Example 3. Benzoic acid could be released from these beads using low concentrations of TFA (1%, 2%, 5%) in $CH_2Cl_2$.

Example 6

EMPHAZE AB 1 beads (25 g) were derivatized by reaction with 300 mL of 1M ethylenediamine in deionized water for 2 hours at room temperature. The derivatized beads were washed with deionized water (2×), 0.1N HCl (2×), 0.0001N HCl, and stored in 20% ethanol/water until needed. Titration indicated the amine content to be 42 µmol of amine per milliliter of beads.

3-Formylindol-1-ylacetic acid was prepared and coupled to the beads above according to the process of EP 0 801 083 A2 (Estep et al.) using diisopropyl carbodiimide, N,N-diisopropylethylamine, and N-hydroxybenzotriazole in DMF/$CH_2Cl_2$. Benzylamine was reductively coupled to this bead-linker using sodium cyanoborohydride in 0.5M acetate buffer, pH 5, by the procedure in the same document. The product was then acetylated using acetic anhydride/triethylamine. The acetylated amine was released from the resin by treatment with 50% TFA/$CH_2Cl_2$ for 4 hours. The filtrate was evaporated to dryness and the residue evaluated by NMR and mass spectroscopy to show that the major product was N-benzylacetamide. This example demonstrates the feasibility of conducting solid phase synthesis using azlactone-functionalized beads.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of solid phase synthesis, the method comprising:
   providing an azlactone-functionalized support;
   reacting an azlactone group of the azlactone-functionalized support with a linker molecule to form a linker-functionalized support having a covalently attached linker group; and
   reacting the linker group of the linker-functionalized support with an organic molecule to form a covalent bond between the linker and the organic molecule; and
   conducting one or more reactions on the covalently bound organic molecule to produce a derivatized organic molecule.

2. The method of claim 1 wherein the covalent bond formed between the linker and the organic molecule can be cleaved under mild conditions.

3. The method of claim 2 wherein mild conditions comprise mild acidic or mild basic conditions.

4. The method of claim 1 further comprising cleaving the derivatized molecule from the linker-functionalized support.

5. The method of claim 1 wherein the organic molecule is a building block for a combinatorial library.

6. The method of claim 1 wherein the derivatized organic molecule is a polypeptide or polynucleotide.

7. The method of claim 1 wherein the linker-functionalized support has the following formula:

$$SS-[C(O)-NH-C(R^5)(R^6)-(CH_2)_n-C(O)-NH-(C(R^1)(R^2))_p-C(R^3)(R^4)(OR^7)]_m$$

wherein:
   SS represents a support material;
   $C(O)-NH-C(R^5)(R^6)-(CH_2)_n-C(O)$ is derived from an azlactone group, wherein $R^5$ and $R^6$ are each independently an organic group and n is 0 to 1;
   $NH-(C(R^1)(R^2))_p-C(R^3)(R^4)(OR^7)$ represents the linker, wherein $R^1$, $R^2$, $R^3$, and $R^4$ are each independently hydrogen or an organic group with the proviso that at least one of $R^3$ and $R^4$ is an aromatic group, $R^7$ is hydrogen, a protecting group, or an organic group capable of being derivatized, and p is at least 1; and
   m is 1 to the resin capacity of the support material;
   and further wherein reacting the linker-functionalized support with an organic molecule occurs at the $-OR^7$ group.

8. The method of claim 7 wherein p is 1 to 20.

9. The method of claim 7 wherein $R^7$ is hydrogen.

10. The method of claim 7 wherein $R^7$ is a protecting group and conducting one or more reactions on the linker attached to the azlactone-functionalized support comprises removing the protecting group.

11. The method of claim 1 wherein the azlactone-functionalized support is in the form of a plurality of particles or a membrane.

12. A method of solid phase synthesis, the method comprising:
providing an amine-modified-azlactone-functionalized support;
reacting the amine-modified-azlactone-functionalized support with a linker molecule to form a linker-functionalized support having a covalently attached linker; and
conducting one or more reactions on the linker-functionalized support.

13. The method of claim 12 wherein conducting one or more reactions on the linker-functionalized support comprises:
reacting the linker-functionalized support with an organic molecule to form a covalent bond between the linker and the organic molecule; and
conducting one or more reactions on the covalently bound organic molecule to produce a derivatized organic molecule.

14. The method of claim 13 wherein the covalent bond formed between the linker and the organic molecule can be cleaved under mild conditions.

15. The method of claim 14 wherein mild conditions comprise mild acidic or mild basic conditions.

16. The method of claim 13 further comprising cleaving the derivatized molecule from the linker-functionalized support.

17. The method of claim 12 wherein the linker-functionalized support has the following formula:

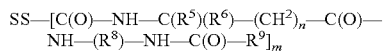

wherein:
SS represents a support material;
$C(O)$—$NH$—$C(R^5)(R^6)$—$(CH_2)_n$—$C(O)$ is derived from an azlactone group, wherein $R^5$ and $R^6$ are each independently an organic group and n is 0 to 1;
$NH$—$(R^8)$—$NH$ is derived from a diamine, wherein $R^8$ is an organic connecting group;
$C(O)$—$R^9$ represents the linker, wherein $R^9$ is an organic group; and
m is 1 to the resin capacity of the support material;
and further wherein reacting the linker-functionalized support with an organic molecule occurs at the —$R^9$ group.

18. A method of solid phase synthesis, the method comprising:
providing a linker-functionalized support having a covalently attached linker, the linker-functionalized support having a formula:

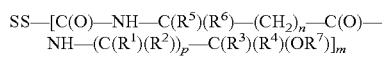

wherein:
SS represents a support material;
$C(O)$—$NH$—$C(R^5)(R^6)$—$(CH_2)_n$—$C(O)$ is derived from an azlactone group, wherein $R^5$ and $R^6$ are each independently an organic group and n is 0 to 1;
$NH$—$(C(R^1)(R^2))_p$—$C(R^3)(R^4)(OR^7)$ represents a linker, wherein $R^1$, $R^2$, $R^3$, and $R^4$ are each independently hydrogen or an organic group with the proviso that at least one of $R^3$ and $R^4$ is an aromatic group, $R^7$ is hydrogen, a protecting group, or an organic group capable of being derivatized, and p is at least 1; and
m is 1 to the resin capacity of the support material; and
conducting one or more reactions on the linker-functionalized support.

19. A method of solid phase synthesis, the method comprising:
providing a linker-functionalized support having a covalently attached linker, the linker-functionalized support formula:

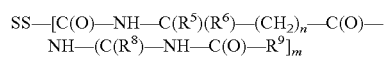

wherein:
SS represents a support material;
$C(O)$—$NH$—$C(R^5)(R^6)$—$(CH_2)_n$—$C(O)$ is derived from an azlactone group, wherein $R^5$ and $R^6$ are each independently an organic group and n is 0 to 1;
$NH$—$(R^8)$—$NH$ is derived from a diamine, wherein $R^8$ is an organic connecting group;
$C(O)$—$R^9$ represents the linker, wherein $R^9$ is an organic group; and
m is 1 to the resin capacity of the support material; and
conducting one or more reactions on the linker-functionalized support.

20. A method of solid phase synthesis, the method comprising:
providing an azlactone-functionalized support;
reacting the azlactone-functionalized support with a linker molecule to form a linker-functionalized support having a linker attached thereto, which has the formula:

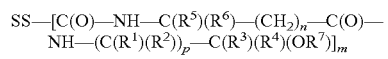

wherein:
SS represents a support material;
$C(O)$—$NH$—$C(R^5)(R^6)$—$(CH_2)_n$—$C(O)$ is derived from an azlactone group, wherein $R^5$ and $R^6$ are each independently an organic group and n is 0 to 1;
$NH$—$(C(R^1)(R^2))_p$—$C(R^3)(R^4)(OR^7)$ represents a linker, wherein $R^1$, $R^2$, $R^3$, and $R^4$ are each independently hydrogen or an organic group with the proviso that at least one of $R^3$ and $R^4$ is an aromatic group, $R^7$ is hydrogen, a protecting group, or an organic group capable of being derivatized, and p is at least 1; and
m is 1 to the resin capacity of the support material;
reacting the linker with an organic molecule to form a covalent bond between the linker and the organic molecule;
conducting one or more reactions on the covalently bound organic molecule to produce a derivatized organic molecule; and
cleaving the derivatized molecule from the linker-functionalized support.

21. A method of solid phase synthesis, the method comprising:
providing an azlactone-functionalized support; reacting the azlactone-functionalized support with a diamine to forma an amine-modified-azlactone-functionalized support;

reacting the amine-modified-azlactone-functionalized support with a linker molecule to form a linker-functionalized support having a covalently attached linker, the linker-functionalized support having the formula:

wherein:
SS represents a support material;
C(O)—NH—C($R^5$)($R^6$)—(CH$_2$)$_n$—C(O) is derived from an azlactone group, wherein $R^5$ and $R^6$ are each independently an organic group and n is 0 to 1;
NH—($R^8$)—NH is derived from the diamine, wherein $R^8$ is an organic connecting group;
C(O)—$R^9$ represents the linker, wherein $R^9$ is an organic group; and
m is 1 to the resin capacity of the support material;
reacting the linker with an organic molecule so as to form a covalent bond between the linker and the organic molecule;
conducting one or more reactions on the covalently bound organic molecule to produce a derivatized organic molecule; and
cleaving the derivatized molecule from the linker-functionalized support.

22. The method of claim 21 wherein C(O)—$R^9$ is derived from 4-hydroxymethylbenzoic acid, 4hydroxymethylphenoxyacetic acid, 4-hydroxymethyl-3-methoxyphenoxybutyric acid, 4-hydroxymethylphenylacetic acid, 4-bromoacetylphenoxyacetic acid, 4-(diphenylhydroxymethyl)benzoic acid, 4-hydroxymethyl-2-methoxy-5-nitrophenoxybutyric acid, phenoxyacetic acid and phenoxybutyric acid analogs of Rink acid and Rink amide linker molecules and Sieber amide linker molecules, 4sulfamylbenzoic acid, 4-sulfamylbutyric acid, 4-formylphenoxyacetic acid, 4-(4-formyl-3-methoxyphenoxy)butyric acid, 4-formyl-3,5-dimethoxyphenoxyacetic acid, or 3-formylindol-1-ylacetic acid.

23. The method of claim 21 wherein NH—($R^8$)—NH is derived from ethylenediamine, 1,3-propanediamine, 1,3-diamino-2-hydroxypropane, or 1,6-hexanediamine.

* * * * *

UNITED STATES PATENT AND TRADEMARK OFFICE
CERTIFICATE OF CORRECTION

PATENT NO.       : 7,166,696 B2
APPLICATION NO.  : 10/900240
DATED            : January 23, 2007
INVENTOR(S)      : Jerald K. Rasmussen It is certified that error appears in the above-identified patent and that said Letters Patent is hereby corrected as shown below:

Col. 2
Line 57, delete "$C(R_5)(R^6)$" and insert -- $C(R^5)(R^6)$ --, therefor.

Col. 3
Line 10, delete "$C(R_5)(R^6)$" and insert -- $C(R^5)(R^6)$ --, therefor.

Col. 4
Line 9, delete "$C(R_5)(R^6)$" and insert -- $C(R^5)(R^6)$ --, therefor.
Line 25, delete "$C(R_5)(R^6)$" and insert -- $C(R^5)(R^6)$ --, therefor.
Line 36, delete "amine-odified" and insert -- amine-modified --, therefor.

Col. 5
Line 14, delete "$C(R_5)(R^6)$" and insert -- $C(R^5)(R^6)$ --, therefor.
Line 34, delete "$C(R_5)(R^6)$" and insert -- $C(R^5)(R^6)$ --, therefor.
Line 40, before "is an" delete "$R^9$" and insert -- $R^8$ --, therefor.
Line 60, delete "embodiments" and insert -- embodiments. --, therefor.
Line 50, delete "he" and insert -- The --, therefor.

Col. 7
Line 5, delete "derivitized" and insert -- derivatized --, therefor.

Col. 9
Line 3, delete "(Heilman" and insert -- (Heilmann --, therefor.
Line 18, delete "derivitized" and insert -- derivatized --, therefor.
Line 25, delete "hydroxylprotecting" and insert
          -- hydroxyl protecting --, therefor. (Consider space)

Col. 10
Line 59, delete "$C(R_5)(R^6)$" and insert -- $C(R^5)(R^6)$ --, therefor.

Col. 11
Line 17, delete "$C(R_5)(R^6)$" and insert -- $C(R^5)(R^6)$ --, therefor.

Col. 12
Lines 39-40, delete "BiORad," and insert -- BioRad, --, therefor.

Col. 15
Line 40, delete "derizatized" and insert -- derivatized --, therefor.

UNITED STATES PATENT AND TRADEMARK OFFICE
CERTIFICATE OF CORRECTION

PATENT NO. : 7,166,696 B2
APPLICATION NO. : 10/900240
DATED : January 23, 2007
INVENTOR(S) : Jerald K. Rasmussen It is certified that error appears in the above-identified patent and that said Letters Patent is hereby corrected as shown below:

Col. 17
Line 35, in Claim 17, delete "—$(CH^2)_n$—" and insert
-- —$(CH_2)_n$— --, therefor.
Line 64, in Claim 18, after "represents" delete "a" and insert
-- the --, therefor.

Col. 18
Line 15, in Claim 19, delete "—$\mathbf{(C(R^8)}$—" and insert
-- —$(R^8)$— --, therefor.
Line 45, in Claim 20, after "represents" delete "a" and insert
-- the --, therefor.
Line 66, in Claim 21, delete "forma" and insert -- form --, therefor.

Signed and Sealed this

Fourteenth Day of August, 2007

JON W. DUDAS
*Director of the United States Patent and Trademark Office*